United States Patent [19]

Noiles

[11] 4,275,813

[45] Jun. 30, 1981

[54] COHERENT SURGICAL STAPLE ARRAY

[75] Inventor: Douglas G. Noiles, New Caanan, Conn.

[73] Assignee: United States Surgical Corporation, Norwalk, Conn.

[21] Appl. No.: 45,289

[22] Filed: Jun. 4, 1979

[51] Int. Cl.³ .............................................. B21D 53/46
[52] U.S. Cl. ........................................ 206/339; 59/71; 128/334 R; 220/DIG. 30; 227/DIG. 1; 428/913; 411/442; 411/457
[58] Field of Search ............. 227/19, DIG. 1; 428/16, 428/913; 260/340.2; 59/71, 75; 85/49; 206/339, 340; 128/334 R, 335; 220/DIG. 30

[56] References Cited

U.S. PATENT DOCUMENTS

| 1,942,249 | 1/1934 | Kleinschmit | 59/71 |
| 2,522,656 | 9/1950 | Whalen | 59/77 |
| 2,853,074 | 9/1958 | Olson | 128/322 |
| 2,874,384 | 2/1959 | Krone | 128/326 X |
| 3,079,608 | 3/1963 | Babkin | 29/509 X |
| 3,225,996 | 12/1965 | Mallina | 227/137 |
| 3,267,660 | 8/1966 | Matthews | 59/77 |
| 3,297,033 | 1/1967 | Schmitt et al. | 128/335.5 |
| 3,463,158 | 8/1969 | Schmitt et al. | 128/334 |
| 3,489,330 | 1/1970 | Mallina et al. | 227/19 |
| 3,597,449 | 8/1971 | DeProspero et al. | 260/340.2 |
| 3,604,561 | 9/1971 | Mallina et al. | 128/334 R X |
| 3,620,218 | 11/1971 | Schmitt et al. | 128/334 R |
| 3,873,016 | 3/1975 | Fishbein | 227/19 X |
| 3,875,937 | 4/1975 | Schmitt et al. | 128/334 R X |

Primary Examiner—Henry F. Epstein
Attorney, Agent, or Firm—Fleit & Jacobson

[57] ABSTRACT

A coherent surgical-staple stack comprising a plurality of staples, bonded together in a parallel contiguous relationship by a biodegradable, absorbable plastic.

23 Claims, 2 Drawing Figures

FIG. 1
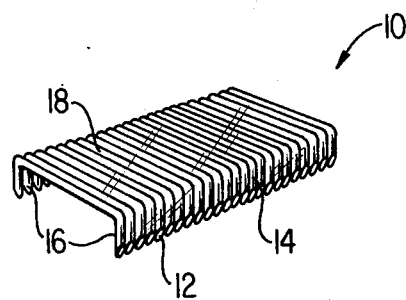
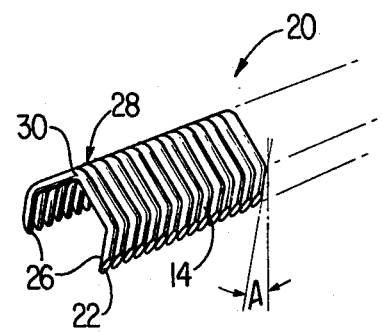
FIG. 2

COHERENT SURGICAL STAPLE ARRAY

BACKGROUND OF THE INVENTION

1. Field of the Invention

This invention relates to a coherent array of surgical staples formed when the staples are bonded together by a biodegradable, absorbable plastic.

2. Description of the Prior Art

Surgical stapling instruments which are actuated repetitively to discharge and form, in sequence, a series of surgical staples one at a time are well known in the art. One type of surgical stapler is used for ligating blood vessels and the like during surgical operations, whereas another type is used for joining together a variety of tissues within the body such as bronchia, intestines, blood vessels and so forth. Still another type is used for joining disunited skin or fascia. Among these types of staplers are those which have in common the method of feeding staples in a stacked array of individual staples, one staple pushing the other.

In some prior art surgical staplers, the stacked array, comprised of individual surgical staples, is mounted in a cartridge for insertion into an instrument. In other prior art staplers, the array of individual surgical staples is mounted within a housing contained in the instrument itself.

Examples of prior art surgical staplers of the type described can be found in U.S. Pat. Nos. 2,853,074, 3,874,384, 3,079,608, 3,225,996, 3,489,330, 3,604,561 and 3,873,016.

In all of the surgical staplers which make use of a stacked staple array, the first staple in the array is pushed out of the cartridge or instrument by a driver which is moved in response to the actuation of the instrument; the staple is clinched against an anvil as the instrument is actuated. After application of the staple, when the instrument is returned to its normal starting condition, a pusher moves the series of staples forward so that the next successive staple in the array will be in position to be applied when the instrument is again actuated.

Except for skin staplers which use the relatively larger diameter wires of 0.020 inch or greater, none of the other surgical staplers have attained significant commercial use. At least one of the reasons why these staplers have not come into common use is that the above-described method of staple-feeding is not entirely reliable. Frequently, surgical staplers are required to feed staples made from very small diameter wire. One prior art stapler contemplates the use of wires having diameters as small as 0.006 inches. Staples made from such small wire must be fed in closely fitted guide grooves within the staple cartridge, or instrument, so that the manufacturing tolerances of both the preformed staple and the guide grooves become extremely critical. If the grooves are too large, the staples move sideways on one another and bind, and generally interfere with smooth feeding. Such interference leads to staple jams, which render the instrument inoperative. Because the instruments are less than reliable for the reason described above, their use has not become widespread.

There is thus a need for an improved staple array which minimizes the problem of staple jams when used in a surgical stapling instrument that relies on a stacked staple array.

SUMMARY OF THE INVENTION

The present invention relates to an improved coherent array of surgical staples for use in a cartridge or stapling instrument. The coherent array or stack of staples comprises a plurality of surgical staples assembled in contiguous parallel relationship and attached or bonded together by a biologically degradable, absorbable plastic.

In one method of producing the coherent staple stack, preformed surgical staples are first coated by a conventional rolling or spraying technique with a solution containing a biocompatible substance. After coating, the staples are arranged in a stacked array, and then the solvent is allowed to evaporate leaving the biologically compatible substance as a film which causes the staples to adhere to each other.

In another method for producing the coherent stacked array of surgical staples, steps similar to those previously described are carried out, except that the solution of the biologically compatible substance is sprayed or rolled onto the staples after they have been arranged in a stacked array.

In yet another method, small diameter wires, made from surgical steel or the like, are coated with a solution of a biologically compatible substance by rolling or spraying, formed into a stacked array of U-shaped surgical staples, after which the solvent is allowed to evaporate leaving a film which binds the staples to one another.

It is, thus, an object of the present invention to provide an improved coherent stacked array of surgical staples for use in a surgical stapling instrument or cartridge.

It is another object of the present invention to provide a coherent stacked array of surgical staples bonded together by a biologically degradable, absorbable plastic.

It is a further object of the present invention to provide a coherent stacked array of surgical staples which greatly decreases the likelihood of staple jams occurring in the feed mechanism of a surgical stapler or cartridge.

Additional objects of the present invention will become apparent from a reading of the appended specification and claims in which preferred, but not necessarily the only, forms of the invention will be described in detail, taken in connection with the drawings accompanying and forming a part of the application.

BRIEF DESCRIPTION OF THE DRAWING

FIG. 1 is a perspective view of a coherent stacked array of surgical staples in accordance with the present invention.

FIG. 2 is a perspective view of yet another coherent stacked array of surgical staples in accordance with the present invention.

DETAILED DESCRIPTION OF THE DRAWING

In describing the preferred embodiments of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

With reference to FIG. 1, a coherent stacked array of surgical staples embodying the subject invention is generally designated as 10. The array comprises a plurality of staples 12 assembled in a contiguous parallel relationship and attached together, one to the other, by a film or coating 14 formed from a biologically compatible plastic material. Each of the staples illustrated in FIG. 1 comprises two legs 16 and a crown 18. It is contemplated that the coating 14 need not cover the entire staple array. For example, the coating 14 may selectively cover only the crown or legs of the staples 12, the primary consideration being that the coating 14 bond the staples together in a contiguous parallel relationship. Further, it should be pointed out that the staples may have other well-known configurations depending on their intended use, again, the main concern being that the staples be arranged to form the coherent stacked array.

Another embodiment of the coherent stacked array of surgical staples is shown in FIG. 2. The array, generally designated as 20, comprises a plurality of staples 22 assembled in a contiguous parallel relationship and bonded together, one to the other, by a film or coating 14 formed from a biologically compatible material. Each of the staples illustrated in FIG. 2 comprises two legs 26 and a crown 28 terminating in an apex 30. The staples are bonded together so that the legs are at an angle to the normal as defined by an angle A that is determined by the configuration of the staple-receiving portion, of the surgical instrument or cartridge in which the array is to be stored.

Any non-toxic plastic may be used for the purposes of this invention. It is preferred, however, that the plastic is also biologically degradable and absorbable within the body.

Known non-absorbable surgically acceptable plastics include, but are not limited to: polyalkylenes such as polyethylene or polypropylene; polyamides such as nylon; polyesters such as polyethylene terephthalate; polyacrylonitriles; or halogenated polyalkylenes such as polytetrafluoroethylene. Non-absorbable plastics are generally acceptable for implantation within the body and, therefore, are an embodiment of this invention. However, such materials are less favored by the medical profession because they may form particles which migrate within the body and the long range result of such migration of a number of particles is, at present, unknown.

Known biologically absorbable and degradable plastics which are suitable include, but are not limited to, polyglycolic acid polymers, all of the polylactic acid stereoisomer polymers, polyglycolic acid-lactic acid copolymers, their homologs and analogs, and mixtures of these polymers.

Conventional adjuvants, such as plasticizers, color stabilizers, and curing agents, may be incorporated with the plastics, where so desired, provided that the resulting plastic composition after curing, is non-toxic.

Curing of the plastics may be by any suitable conventional means, including but not limited to, heat, U.V. radiation, and actinic radiation.

The plastic may be applied to the array of staples by coating the array with a brush or roller, spraying the array, or dipping the array into the plastic. Depending upon the requirements of the method of application, the plastic may be applied per se, or as a solution of varied viscosity, using a suitable organic solvent, such as dioxane, methylene chloride, acetone, tertiary alcohols, and the like. Although any polymer solvent may be used, it must be present in a non-toxic amount or removed during the curing of the polymer. After application, the polymer is cured and the solvent is evaporated to leave an array of staples bonded together by the plastic.

Discussions of biodegradable polymers which may be useful in this invention can be found in U.S. Pat. Nos. 3,297,033, filed Oct. 31, 1963; 3,463,158, filed Jan. 9, 1967; 3,597,449, filed Nov. 16, 1967; 3,620,218, filed Aug. 25, 1969; and 3,875,937, filed May 31, 1973.

For bonding the surgical staples 12 to form the staple array 10, a particularly useful polymer composition is a solution of 1 part of 90% d, 1-polylactic acid with 10% polyglycolic acid, dissolved in 6 parts of dioxane. When cured, it is believed that a copolymer is formed. The L+polylactic acid stereoisomer is also particularly useful in forming a copolymer with polyglycolic acid.

A coherent stacked array of staples prepared in accordance with the above teaching may be used in any of the prior art surgical staplers which employ such an array, and will greatly improve the reliability of the feeding function. The stack of staples is stable and will feed reliably in a guide mechanism with less critical tolerance requirements than would be the case where the staples are not joined to one another. Since the amount of material delivered is small, and is absorbable by the body, any of the polymer or copolymer adhering to the staple delivered to the surgical site or particles falling into the surgical field are of minor consequence. The material does not contribute to the strength or grip of the tissue by the formed wire staple.

In one method for making the coherent surgical staple stack, a plurality of preformed surgical staples are coated by a conventional rolling or spraying technique with a solution of a biologically degradable, absorbable plastic, such as the combination of ingredients referred to hereinbefore. Before evaporation of the dioxane solvent has taken place, the coated staples are arranged in a parallel contiguous relationship. The solvent is then allowed to evaporate to yield the coherent staple stack of the present invention.

In another method, individual wires are coated by rolling or spraying with the solution of the biologically degradable, absorbable plastic and then arranged in a parallel contiguous relationship before curing. The wires, arranged on a suitable mandrel, are then shaped into staples after which the solvent is evaporated, thus, yielding the coherent staple stack.

In yet another method for producing the coherent array of surgical staples, preformed staples are first arranged in a parallel contiguous relationship and then coated by a conventional rolling or spraying technique with the solution of the biologically degradable, absorbable plastic, such as the combination of ingredients referred to hereinbefore. The solvent is then caused to evaporate, as by a suitable application of heat and ventilation, to yield to coherent staple stack of the present invention.

Obviously, many modifications and variations of the present invention are possible in light of the above teachings and it is contemplated that, within the scope of the appended claims, the invention may be practiced otherwise than as specifically described.

I claim:
1. A coherent surgical-staple stack comprising:
   a plurality of individual, deformable surgical staples, each of said staples including a pair of legs joined together at one end by a crown, said staples ar- ranged one next to the other in a contiguous parallel array with any two adjacent staples having their legs and crowns touching; and a film made from a biologically compatible non-toxic material, said film being disposed between adjacent staples in said array for bonding said adjacent staples one to the other.

2. The stack of claim 1, wherein said material is biologically degradable and absorbable in the body.

3. The stack of claim 2, wherein said material is a synthetic polymer.

4. The stack of claim 3, wherein said polymer comprises polyglycolic acid.

5. The stack of claim 3, wherein said polymer comprises polylactic acid.

6. The stack of claim 3, wherein said material comprises a copolymer of polylactic and polyglycolic acids.

7. The stack of claim 6, wherein said biologically compatible material comprises a copolymer of 90% polylactic acid with 10% polyglycolic acid.

8. The stack of claim 7, wherein the polylactic acid is primarily the L+stereoisomer.

9. The stack of claim 1, wherein said material is biodegradable.

10. A coherent surgical-staple stack comprising:

a plurality of individual deformable surgical staples, each of said staples including a pair of legs joined together at one end by a crown, said staples arranged one next to the other in a contiguous parallel array with any two adjacent staples having their similar legs and crowns touching, and a biodegradable, absorbable plastic disposed about adjacent staples for securing said adjacent staples one to the other.

11. For use in a surgical stapling instrument that deforms individual surgical staples in the act of stapling disunited tissue, a coherent stack of staples comprising:

a plurality of individual deformable surgical staples arranged in a parallel contiguous relationship, and a biologically compatible material securing said staples one to the other.

12. The stack of claim 11, wherein said material is biologically degradable.

13. The stack of claim 11, wherein said material is absorbable in the body.

14. The stack of claim 11, wherein said material is a synthetic absorbable polymer.

15. The stack of claim 14, wherein said polymer is made from polyglycolic acid.

16. The stack of claim 14, wherein said polymer is made from polylactic acid.

17. The stack of claim 14, wherein said polymer comprises a copolymer of polylactic and polyglycolic acid.

18. The stack of claim 17, wherein said biologically compatible material comprises a copolymer of 90% L+lactic acid with 10% glycolic acid.

19. The stack of claim 1, wherein said surgical staples are made of metal.

20. The stack of claim 11, wherein said surgical staples are made of metal.

21. A coherent surgical-staple stack comprising:

a plurality of individual deformable metal surgical staples, each of said staples including a pair of legs spaced from each other and joined together at one end by a crown, said staples arranged one next to the other in a contiguous parallel array with any two adjacent staples having their similar legs and crowns touching; and a film made from a biologically compatible non-toxic material, said film being disposed about adjacent staples in said array for bonding said adjacent staples one to the other.

22. The stack of claim 21, wherein said film is confined to an area between the crowns of adjacent staples.

23. The stack of claim 21, wherein said film is confined to the areas between the legs of adjacent staples.

* * * * *